United States Patent
Abu-Jdayil et al.

(10) Patent No.: US 12,343,432 B2
(45) Date of Patent: Jul. 1, 2025

(54) ENCAPSULATED PROBIOTIC (71) Applicant: UNITED ARAB EMIRATES UNIVERSITY, Al Ain (AE)

(72) Inventors: Basim Abu-Jdayil, Al Ain (AE); Mutamed Ayyash, Al Ain (AE); Asmaa Samir Alhamayda, Al Ain (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 0 days.

(21) Appl. No.: 18/219,623

(22) Filed: Jul. 7, 2023

(65) Prior Publication Data

US 2025/0009669 A1 Jan. 9, 2025

(51) Int. Cl.
| | |
|---|---|
| *A61K 9/48* | (2006.01) |
| *A61K 35/741* | (2015.01) |
| *A61K 35/744* | (2015.01) |
| *A61K 35/745* | (2015.01) |
| *A61K 35/00* | (2006.01) |

(52) U.S. Cl.
CPC .......... *A61K 9/4866* (2013.01); *A61K 9/4833* (2013.01); *A61K 9/4875* (2013.01); *A61K 35/744* (2013.01); *A61K 2035/115* (2013.01)

(58) Field of Classification Search
CPC .. A61K 9/4866; A61K 9/4833; A61K 9/4875; A61K 35/744; A61K 2035/115
See application file for complete search history.

(56) References Cited

U.S. PATENT DOCUMENTS

| | | | |
|---|---|---|---|
| 6,706,287 B2 | 3/2004 | Ranganathan et al. | |
| 8,492,124 B2 * | 7/2013 | Ritter | A23L 33/21 |
| | | | 435/252.1 |
| 2007/0048295 A1 | 3/2007 | Chen et al. | |
| 2011/0008493 A1 | 1/2011 | Zorea | |
| 2011/0200668 A1 * | 8/2011 | Dikovskiy | A61P 1/00 |
| | | | 424/475 |
| 2014/0023693 A1 * | 1/2014 | Guenzburg | A61K 35/742 |
| | | | 424/439 |
| 2016/0192689 A1 | 7/2016 | Horn | |
| 2022/0062141 A1 | 3/2022 | Huang | |

FOREIGN PATENT DOCUMENTS

ES 2350436 A1 11/2011

OTHER PUBLICATIONS

Making Gel Beads ([online] retrieved on Sep. 14, 2023 from: https://smile.oregonstate.edu/sites/smile.oregonstate.edu/files/gel_beads_1.pdf; 4 pages). (Year: 2023).*
Al-Thubiani et al. (Journal of Pure and Applied Microbiology, Dec. 2017; vol. 11(4): 1675-1686) (Year: 2017).*
Frent et al. (Int. J. Mol. Sci. 2022; 23: 24 pages) (Year: 2022).*
Jalali-Jivan, M. et all., "Microemulsions as nano-reactors for the solubilization, separation, purification and encapsulation of bioactive compounds," Advances in Colloid and Interface Science 283:102227 (2020).

* cited by examiner

*Primary Examiner* — Ernst V Arnold
(74) *Attorney, Agent, or Firm* — Nath, Goldberg & Meyer; Joshua B. Goldberg (57) ABSTRACT

An encapsulated probiotic is provided. The encapsulated probiotic includes one or more beneficial bacteria encapsulated in a capsule comprising ground date seeds (pits) and sodium alginate.

19 Claims, 6 Drawing Sheets

ENCAPSULATED PROBIOTIC

BACKGROUND

1. Field

The disclosure of the present patent application relates to an encapsulated probiotic and, particularly, to an encapsulated probiotic including date seed (pit) powder.

2. Description of the Related Art

According to the Food and Agricultural Organization (FAO), 1.3 billion tons of various foods are wasted annually along the supply chain, which could feed up to two billion people without having any further negative effects on the environment. In many nations around the world, the buildup of agricultural industry wastes is regarded as a serious environmental issue. This is especially true for plants where there are no waste recycling facilities. For example, date pits were traditionally either thrown away or used as animal feed, a practice that is still widely used today. Date seeds are considered a type of dry waste because they are large and lightweight (i.e., low density and quality). When date seeds accumulate in large quantities, however, they become a serious problem. Therefore, it is crucial to figure out how to incorporate these wastes into green and sustainable engineering.

Recent developments in the food industry include experimentation with encapsulating various ingredients, including probiotics. Extrusion is one type of encapsulation process, where a hydrocolloid solution is simply made, microorganisms are added to it, and then the cell suspension is extruded through a syringe needle in the form of droplets to fall freely into a hardening solution. The simplicity, ease, low cost, and gentle formulation conditions that guarantee high retention of cell viability when using biopolymers like sodium alginate make this method particularly popular.

Care must be taken when selecting the polymeric mixture of the encapsulated microorganism. Alginate is one of the most common encapsulation matrixes used by researchers. Alginate is an excellent probiotic carrier and aids in probiotic survival. Some studies have found specific drawbacks to using alginate alone in the probiotic encapsulation process. They have mentioned that although the beads, which are made out of alginate, are useful for protecting probiotics during storage, they are not able to do the same in low pH conditions such as in gastrointestinal fluids of the stomach. (OBEROI, K. et al., "Effect of Alginate-Microencapsulated Hydrogels on the Survival of *Lactobacillus rhamnosus* under Simulated Gastrointestional Conditions", Foods 10(9): 10091999 (August 2021))

Thus, an encapsulated probiotic solving the aforementioned problems is desired.

SUMMARY

The encapsulated probiotic includes a composition comprising one or more beneficial bacteria encapsulated in a capsule made from a mixture of ground date seeds (pits) and sodium alginate. The ratio of ground date seeds to sodium alginate may range from 1:4 to 2:1 and the composition may be formulated for oral administration as a probiotic composition.

In an embodiment, the encapsulated probiotic may be made by drying date seeds (pits), grinding the dried date seeds to obtain date seed powder, mixing one or more beneficial bacteria with water to produce a first aqueous mixture, adding the date seed powder and sodium alginate to the first aqueous mixture to produce a second aqueous mixture, and dripping the second aqueous mixture into calcium chloride to form the encapsulated probiotic.

In some embodiments, the date seeds may be date seeds obtained from a particular variety of date plant, which may be selected from the group consisting of Naptit saif, Lulu, Raziz, Naghal, and Khadrawy.

In some embodiments, the ratio of date seed powder to sodium alginate may range from 1:4 to 2:1. The ratio of date seed powder to sodium alginate may be 1:2 when the date powder is obtained from Raziz, Naghal, or Khadrawy dates. The ratio of date seed powder to sodium alginate may be 1:1 when the date powder is obtained from Lulu dates. The ratio of date seed powder to sodium alginate may be 1:4 when the date powder is obtained from Naptit saif dates.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The use of the term "probiotic" refers to a live microorganism that provides some health benefit when consumed. The health benefit may include improving or restoring gut microbiota. Commonly known probiotics include *Leuconostoc* spp., *Lactobacillus* spp., *Pediococcus* spp., *Weissella* spp., *Bifidobacterium bifidum*, *Streptococcus thermophilus*, and *Lactococcus lactis*. The term "lactic acid bacteria" may also be used to refer to a subgroup of probiotics.

The encapsulated probiotic includes a composition comprising one or more beneficial bacteria encapsulated in a capsule made from a mixture of ground date seeds and sodium alginate. The ratio of ground date seeds to sodium alginate may range from 1:4 to 2:1 and the composition may be formulated for oral administration as a probiotic composition.

The beneficial bacteria may be any probiotic bacterium, or any other bacterium having a desired beneficial effect. In some embodiments, the probiotic bacterium may include a bacterium selected from the group consisting of *Leuconostoc* spp., *Lactobacillus* spp., *Pediococcus* spp., *Weissella* spp., *Bifidobacterium bifidum*, *Streptococcus thermophilus*, and *Lactococcus lactis*. In a particular embodiment, the probiotic bacterium may include *Streptococcus thermophilus*.

In an embodiment, the encapsulated probiotic may be made by drying date seeds (pits), grinding the dried date seeds to obtain date seed powder, mixing one or more beneficial bacteria with water to produce a first aqueous mixture, adding the date seed powder and sodium alginate to the first aqueous mixture to produce a second aqueous mixture, and dripping the second aqueous mixture into calcium chloride to form the encapsulated probiotic.

In some embodiments, the date seeds may be date seeds obtained from a particular variety of date plant, which may be selected from the group consisting of Naptit saif, Lulu, Raziz, Naghal, and Khadrawy.

In some embodiments, the ratio of date seed powder to sodium alginate may range from 1:4 to 2:1. The ratio of date seed powder to sodium alginate may be 1:2 when the date powder is obtained from Raziz, Naghal, or Khadrawy dates. The ratio of date seed powder to sodium alginate may be 1:1 when the date powder is obtained from Lulu dates. The ratio of date seed powder to sodium alginate may be 1:4 when the date powder is obtained from Naptit saif dates.

Figure 2:
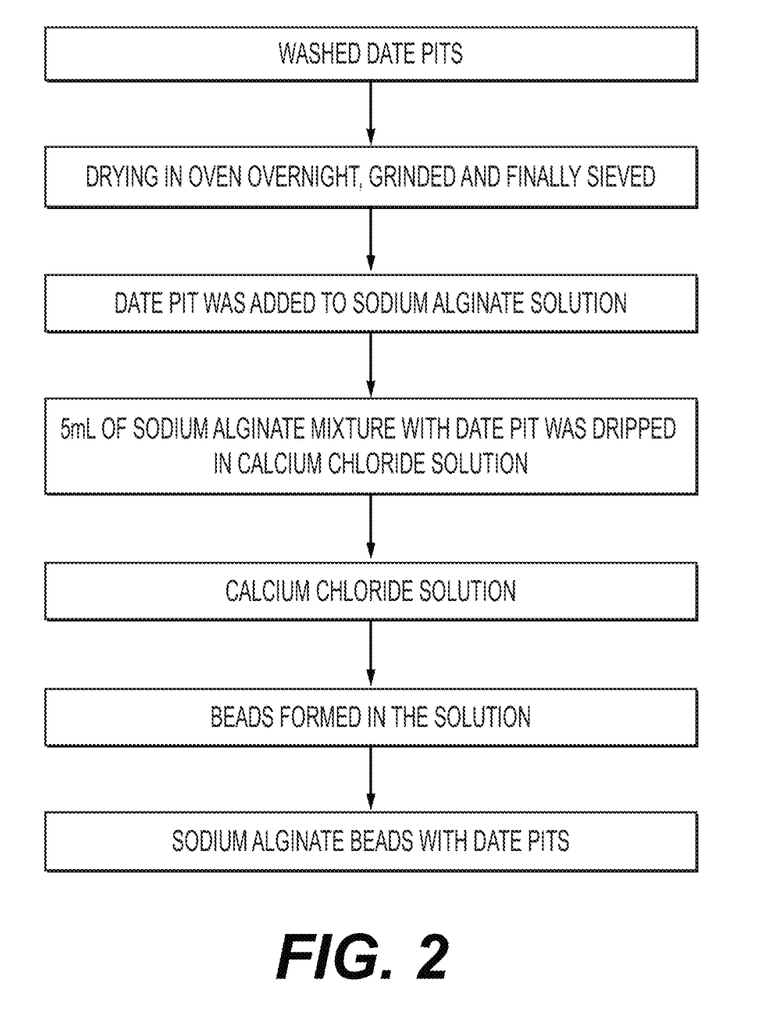
FIG. 2 depicts a flow chart of a method of making the encapsulated probiotic.

As illustrated in FIG. 2, the encapsulated probiotic may be made by extracting date seeds (pits) from dates, cleaning the dates seeds using water and air drying, drying the date seeds in an air drying oven at about 80° C., grinding the dried date seeds with a commercial mixer to obtain date seed powder having an average particle size of about 150 µm, mixing one or more beneficial bacteria with water to produce a first aqueous mixture, adding the date seed powder and sodium alginate to the first aqueous mixture to produce a second aqueous mixture, and dripping the second aqueous mixture into calcium chloride to form the encapsulated probiotic. In certain embodiments, the step of drying the date seeds in an air drying oven may occur for about 48 hours. The step of mixing the one or more beneficial bacteria may be performed with distilled water, under sterilized conditions. Prior to the mixing step, the bacteria may be activated in broth overnight, centrifuged, and resuspended in a buffer solution with a pH of about 7.

The present disclosure may be better understood in view of the following Example.

Example 1

Making Encapsulated Probiotics with Date Seed Powder and Sodium Alginate

Date seeds (pits) were extracted from dates of the Naptit saif, Lulu, Raziz, Naghal, and Khadrway varieties. The date seeds were then cleaned using water and air dried for about a week. The air-dried date seeds were then further dried in an air-drying oven at about 80° C. for about 48 hours and ground with a commercial milling machine and sieved to obtain date seed powder having an average particle size of about 150 μm.

A culture of *Streptococcus thermophilus* (100 μl frozen stock solution) was activated in MRS broth overnight, centrifuged, and resuspended in about 250 μl of a phosphate buffer solution with a pH of about 7. This beneficial bacterium was then mixed with water to produce a first aqueous mixture, and date seed powder and sodium alginate (Sigma-Aldrich, USA) were added to the first aqueous mixture to produce a second aqueous mixture. Separate samples were prepared for each variety of date seed used to test ratios of date seed powder to sodium alginate of 1:4, 1:2, 1:1, and 2:1 (by weight). For each date variety, either 0 g, 0.05 g, 0.1 g, 0.2 g, or 0.4 g date seed powder was mixed with 0.2 g sodium alginate and 500 μl of the first aqueous mixture.

Figure 1A:
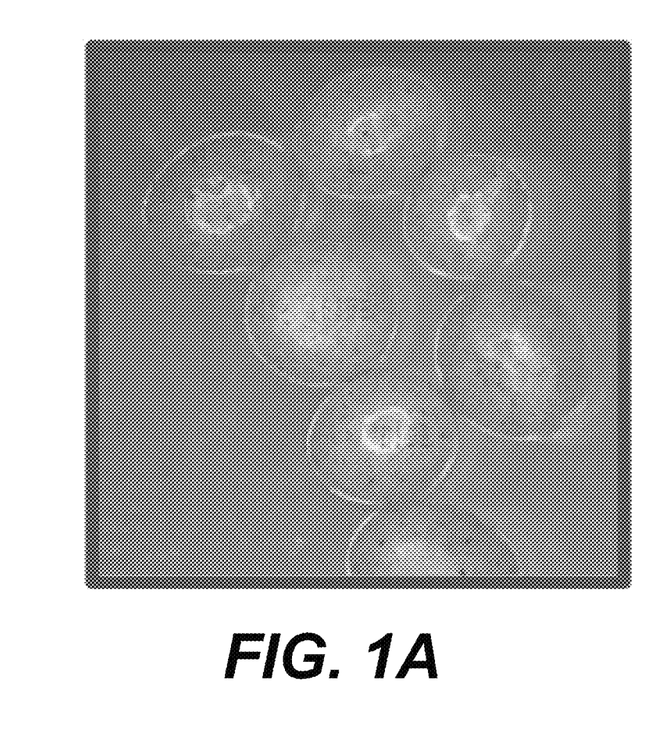
FIGS. 1A-1B depict encapsulated probiotic beads.
Figure 1B:
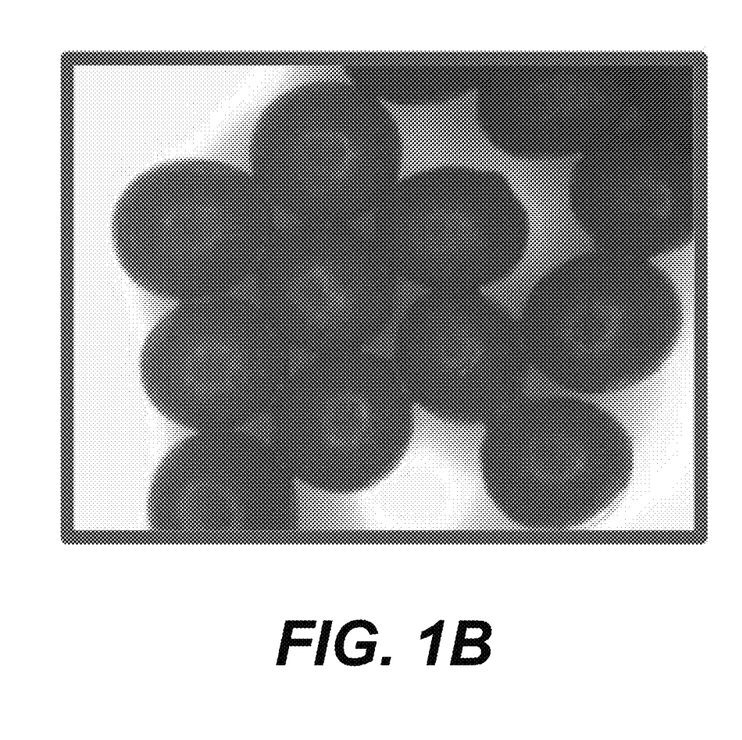

The second aqueous mixture was then dripped into 6% hydrated calcium chloride solution to form the encapsulated probiotic in the form of beads (See FIGS. 1A-1B). The beads were allowed to cure for about 15 minutes and then recovered through a filter paper (Whatman 42, 15 cm, England) and washed with distilled water three times to ensure the removal of any excess $CaCl_2$).

The resulting encapsulated probiotic compositions (along with free cells of *Streptococcus thermophilus* and *Streptococcus thermophilus* encapsulated by sodium alginate alone) were then subjected to an in vitro model of digestion. The digestion protocol first published by COST INFOGEST (Brodkorb, A., "INFOGEST static in vitro simulation of gastrointestinal food digestion", Nature Protocols 14: pp. 991-1014 (2019)) was followed to simulate the oral, gastric, and intestinal exposure phases. Briefly, the samples were held at 37° C. for 2 min., at a pH of 7, and exposed to SSF (Simulated Salivary Fluids), $CaCl_2$), and salivary amylase to simulate the oral stage; followed by being held at 37° C. for 2 min., at a pH of 3, and exposed to SGF (Simulated Gastric Fluids), $CaCl_2$), and pepsin, to simulate the gastric stage; followed by being held at 37° C. for 2 min., at a pH of 7, and exposed to SIF (Simulated Intestinal Fluids), $CaCl_2$), and bile pancreatin to simulate the intestinal stage.

Figure 3:
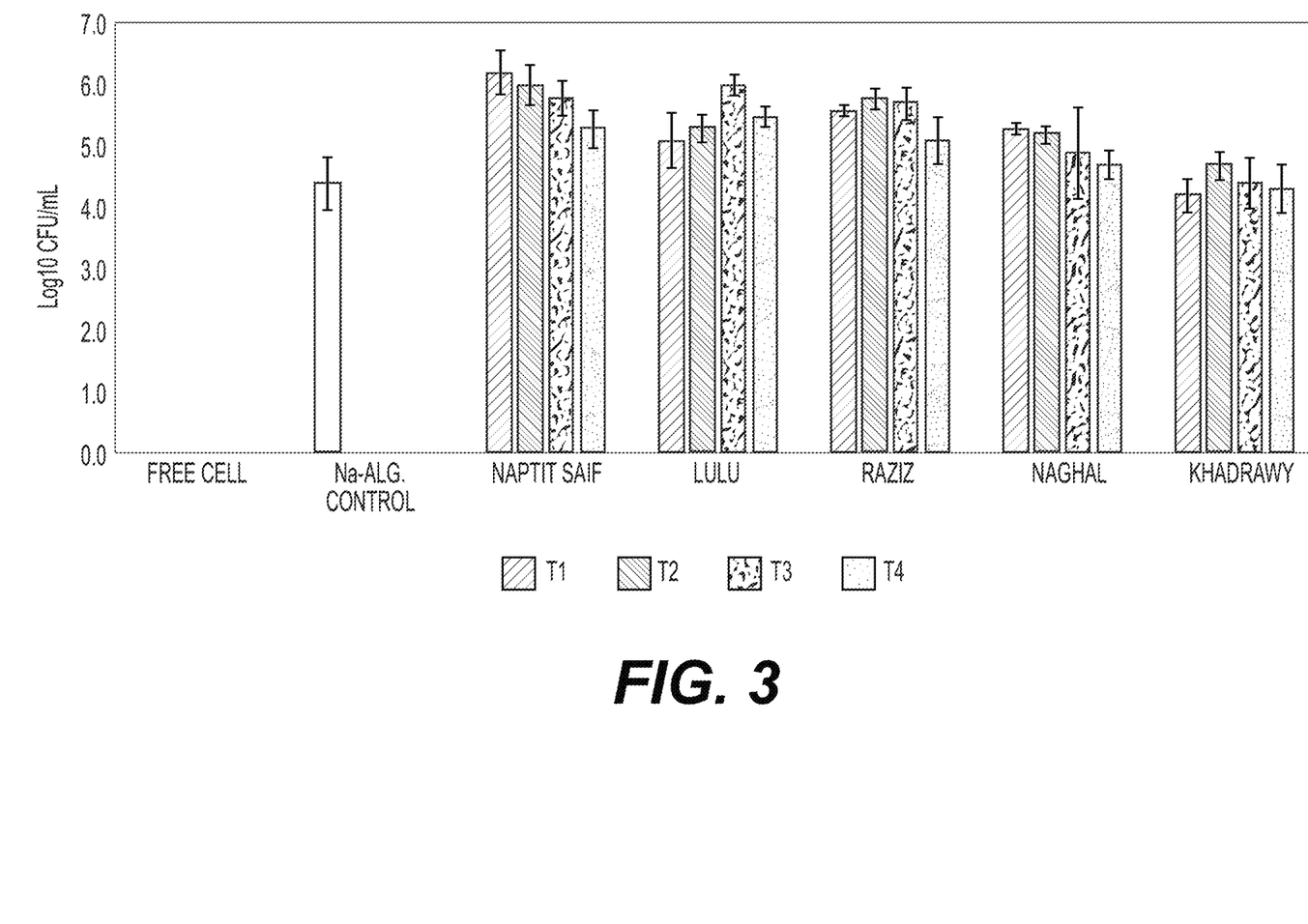
FIG. 3 depicts a graph illustrating the viability of unencapsulated bacteria, bacteria encapsulated in sodium alginate alone, and bacteria encapsulated in a mixture of date seed and sodium alginate, separated by the species of date seed used.
Figure 4:
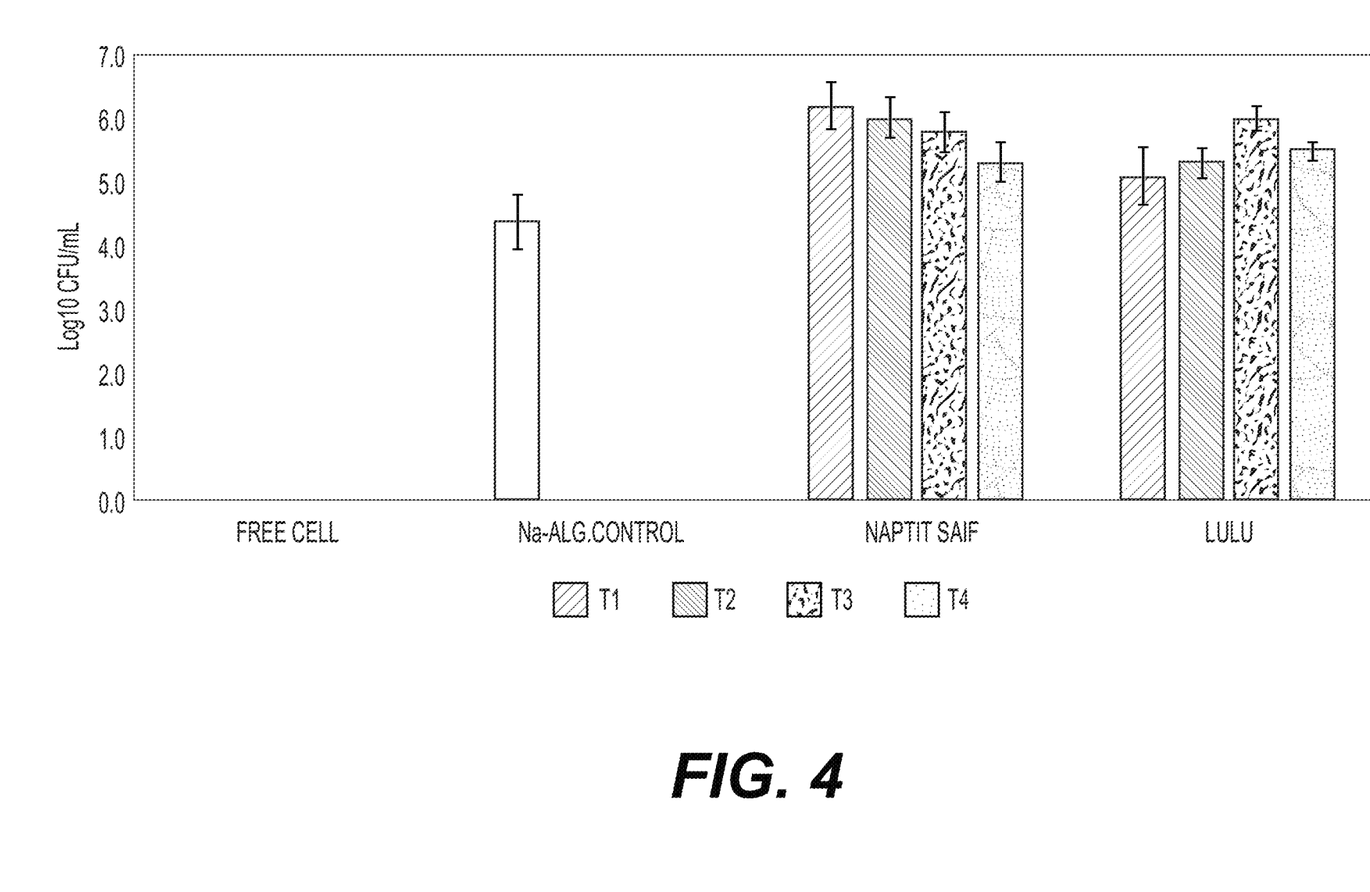
FIG. 4 depicts a graph illustrating the viability of unencapsulated bacteria, bacteria encapsulated in sodium alginate alone, and bacteria encapsulated in a mixture of sodium alginate and either ground Naptit saif date seeds or ground Lulu date seeds.

It was observed that free cells did not survive after the simulated digestion experiment, which provides strong evidence of the importance of encapsulation technology to protect the probiotic from harsh conditions of the human body, especially the low pH of the gastric phase and the bile salt activity of the intestinal phase (See FIG. 3). Another finding in this study was that mixing the sodium alginate with date seed, especially the Naptit Saif and Lulu date seed, increases the stability of the beads (encapsulated probiotic), as the tested compositions showed $Log_{10}$ 6.2 CFU/mL and $Log_{10}$ of 6.0 CFU/mL respectively, compared to using sodium alginate alone as a polymer matrix in encapsulation process which shows a viability of $Log_{10}$ of 4.4 CFU/mL (see FIGS. 3-4).

Figure 5:
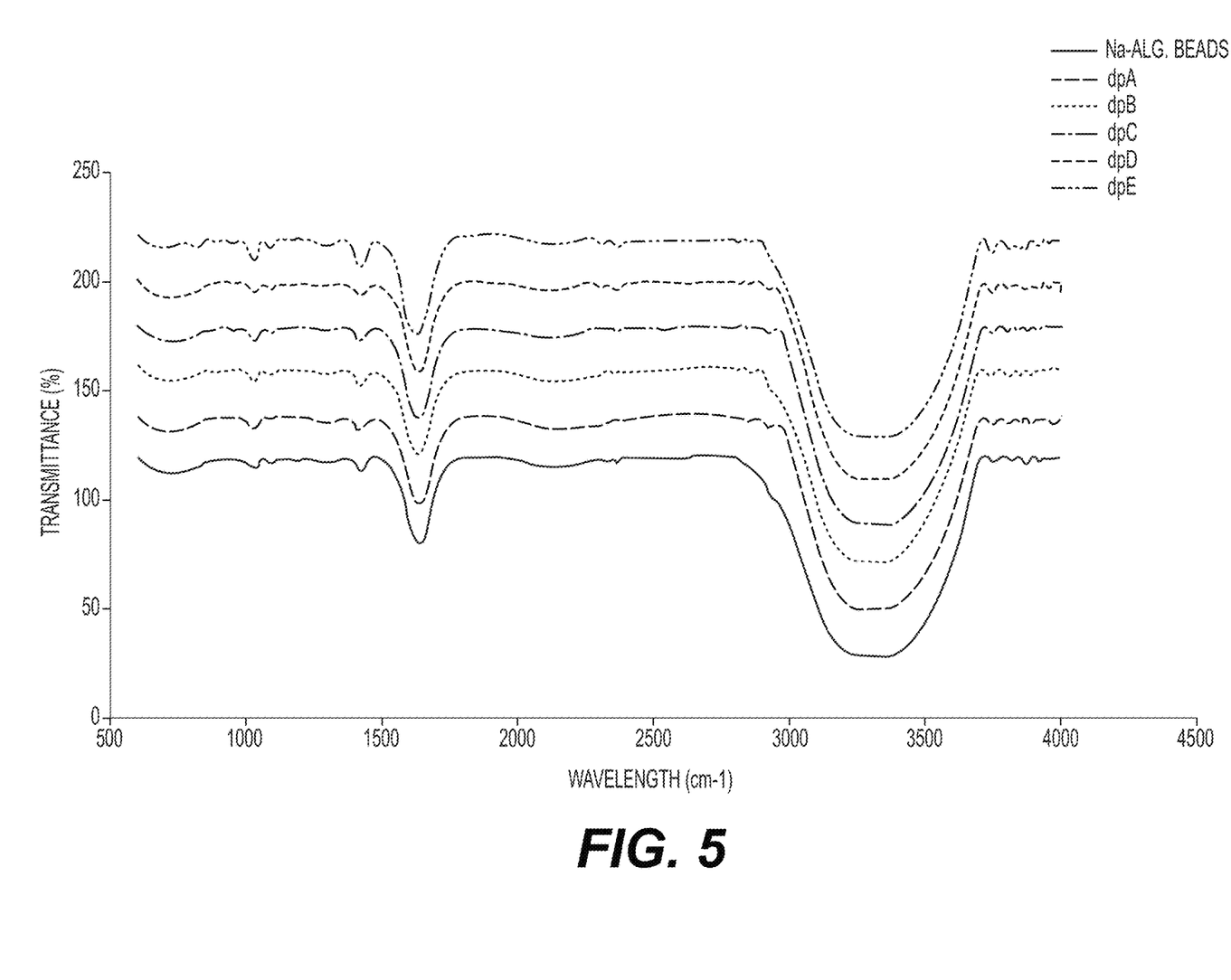
FIG. 5 depicts FTIR analysis of the bacteria encapsulated in sodium alginate alone, and bacteria encapsulated in a mixture of date seed and sodium alginate, separated by the species of date seed used.
Figure 6:
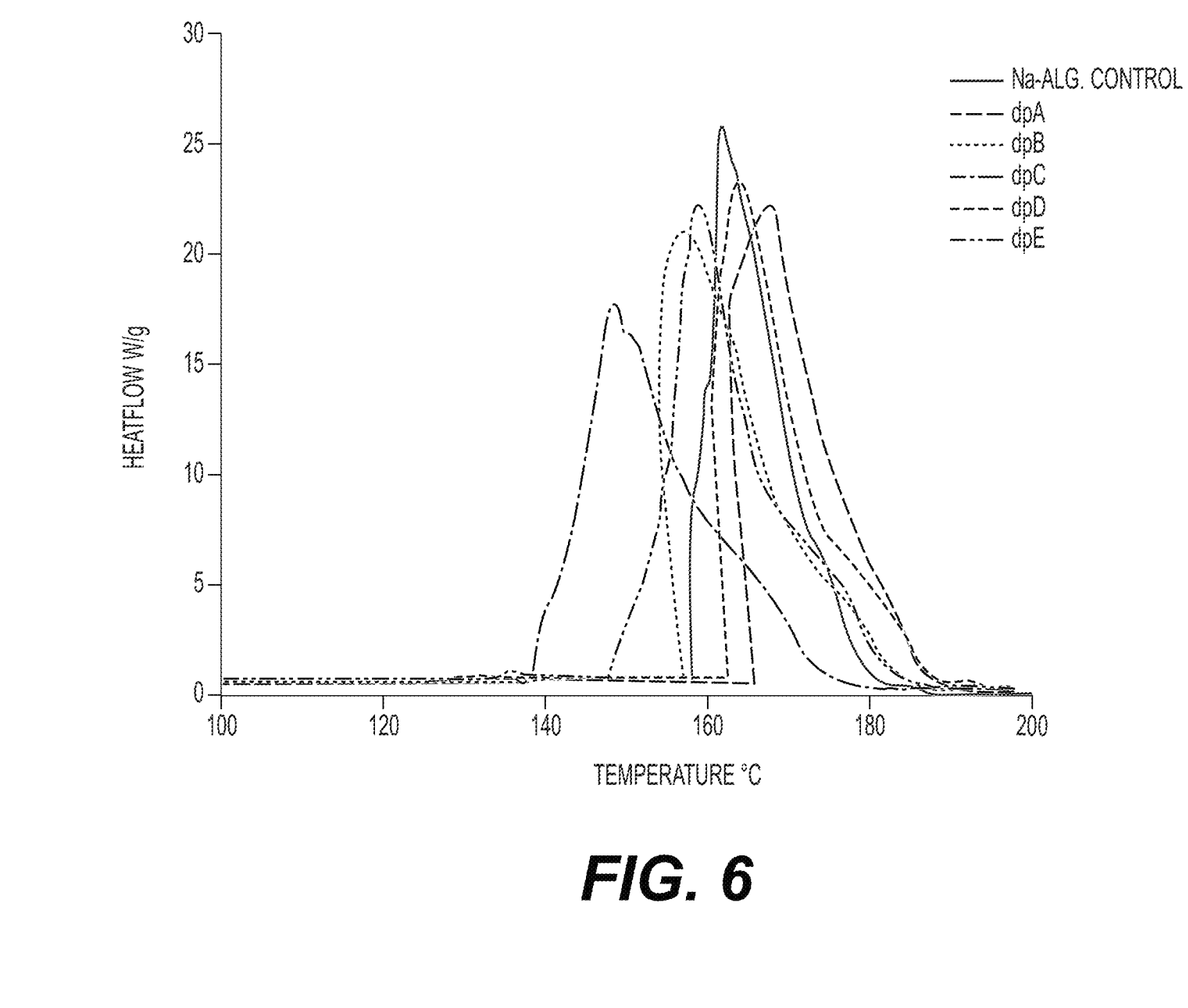
FIG. 6 depicts DSC analysis of bacteria encapsulated in sodium alginate alone, and bacteria encapsulated in a mixture of date seed and sodium alginate, separated by the species of date seed used.

Finally, FTIR and DSC analysis confirmed that the date seed-based beads did not have any new chemical properties when compared to sodium alginate alone (which is generally understood to be safe for human consumption) and thus the date seed-based beads are expected to be safe for human consumption as well (See FIGS. 5-6).

It is to be understood that the encapsulated probiotic is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. An encapsulated probiotic composition comprising at least one beneficial bacterium encapsulated in a mixture of sodium alginate, calcium chloride, and date seed powder; wherein the date seed powder has an average particle size of about 150 μm; and
    wherein the encapsulated probiotic composition has improved stability when compared to a probiotic composition encapsulated in sodium alginate without date seed powder.

2. The encapsulated probiotic composition of claim 1, wherein the at least one beneficial bacterium is selected from the group consisting of *Leuconostoc* spp., *Lactobacillus* spp., *Pediococcus* spp., *Weissella* spp., *Bifidobacterium bifidum*, *Streptococcus thermophilus*, and *Lactococcus lactis*.

3. The encapsulated probiotic composition of claim 1, wherein the at least one beneficial bacterium comprises *Streptococcus thermophilus*.

4. The encapsulated probiotic composition of claim 1, wherein the date seed powder comprises powdered date seeds obtained from at least one variety of date selected from the group consisting of Naptit saif, Lulu, Raziz, Naghal, and Khadrway dates.

5. The encapsulated probiotic composition of claim 1, comprising a ratio of date seed powder to sodium alginate of between about 1:4 and about 2:1 by weight.

6. The encapsulated probiotic composition of claim 1, wherein the date seed powder comprises powdered date seeds obtained from Naptit saif dates and the ratio of date seed powder to sodium alginate is about 1:4 by weight.

7. The encapsulated probiotic composition of claim 1, wherein the date seed powder comprises powdered date seeds obtained from Lulu dates and the ratio of date seed powder to sodium alginate is about 1:1 by weight.

8. The encapsulated probiotic composition of claim 1, wherein the date seed powder comprises powdered date seeds obtained from Raziz dates and the ratio of date seed powder to sodium alginate is about 1:2 by weight.

9. The encapsulated probiotic composition of claim 1, wherein the date seed powder comprises powdered date seeds obtained from Naghal dates and the ratio of date seed powder to sodium alginate is about 1:2 by weight.

10. The encapsulated probiotic composition of claim 1, wherein the date seed powder comprises powdered date seeds obtained from Khadrawy dates and the ratio of date seed powder to sodium alginate is about 1:2 by weight.

11. A method of making an encapsulated probiotic, consisting of:
    a.) drying date seeds;
    b.) grinding the dried date seeds to obtain date seed powder;
    c.) mixing one or more beneficial bacteria with water to produce a first aqueous mixture;
    d.) adding the date seed powder and sodium alginate to the first aqueous mixture to produce a second aqueous mixture; and e.) dripping the second aqueous mixture into calcium chloride to form the encapsulated probiotic composition;

wherein the dried date seeds are ground with a commercial mixer to obtain date seed powder having an average particle size of about 150 µm; and wherein the encapsulated probiotic has improved stability when compared to a probiotic encapsulated in sodium alginate without date seed powder.

12. The method as recited in claim 11, wherein the date seeds are dried in an air drying oven at about 80° C.

13. The method as recited in claim 11, wherein the date seeds are obtained from a variety of dates selected from the group consisting of Naptit saif, Lulu, Raziz, Naghal, and Khadrawy.

14. The method as recited in claim 11, wherein a ratio of the date seed powder and the sodium alginate is between about 1:4 and 2:1 by weight.

15. The method as recited in claim 11, wherein
the date seeds are obtained from Naptit saif dates; and
a ratio of the date seed powder and the sodium alginate added to the first aqueous mixture is about 1:4 by weight.

16. The method as recited in claim 11, wherein
the date seeds are obtained Lulu dates; and
a ratio of the date seed powder and the sodium alginate added to the first aqueous mixture is about 1:1 by weight.

17. The method as recited in claim 11, wherein
the date seeds are obtained from Raziz dates; and
a ratio of the date seed powder and the sodium alginate added to the first aqueous mixture is about 1:2 by weight.

18. The method as recited in claim 11, wherein
the date seeds are obtained from Naghal dates; and
a ratio of the date seed powder and the sodium alginate added to the first aqueous mixture is about 1:2 by weight.

19. The method as recited in claim 11, wherein
the date seeds are obtained from Khadrawy dates; and
a ratio of the date seed powder and the sodium alginate added to the first aqueous mixture is about 1:2 by weight.

* * * * *